United States Patent
Le et al.

(10) Patent No.: US 9,867,548 B2
(45) Date of Patent: Jan. 16, 2018

(54) SYSTEM AND METHOD FOR PROVIDING AND AGGREGATING BIOSIGNALS AND ACTION DATA

(71) Applicant: Emotiv Lifesciences Inc., San Francisco, CA (US)

(72) Inventors: Tan Le, San Francisco, CA (US); Geoff Mackellar, San Francisco, CA (US)

(73) Assignee: Emotiv, Inc., San Francisco, CA (US)

( * ) Notice: Subject to any disclaimer, the term of this patent is extended or adjusted under 35 U.S.C. 154(b) by 1110 days.

(21) Appl. No.: 13/903,806

(22) Filed: May 28, 2013

(65) Prior Publication Data

US 2013/0317382 A1    Nov. 28, 2013

Related U.S. Application Data

(60) Provisional application No. 61/679,044, filed on Aug. 2, 2012, provisional application No. 61/652,040, filed on May 25, 2012.

(51) Int. Cl.

| | |
|---|---|
| *G01N 33/58* | (2006.01) |
| *A61B 5/04* | (2006.01) |
| *A61B 5/0482* | (2006.01) |
| *G06G 7/58* | (2006.01) |
| *A61B 5/00* | (2006.01) |
| *A61B 5/0205* | (2006.01) |
| *G06F 19/00* | (2011.01) |

(52) U.S. Cl.
CPC .............. *A61B 5/04* (2013.01); *A61B 5/0482* (2013.01); *A61B 5/486* (2013.01); *A61B 5/0205* (2013.01); *A61B 5/7285* (2013.01); *G06F 19/34* (2013.01)

(58) Field of Classification Search
CPC ........ G01N 19/18; G01N 19/20; G01N 19/22; G01N 19/32; G01N 33/582
See application file for complete search history.

(56) References Cited

U.S. PATENT DOCUMENTS

| | | | |
|---|---|---|---|
| 4,421,122 A | 12/1983 | Duffy | |
| 6,230,049 B1 | 5/2001 | Fischell et al. | |
| 6,954,700 B2 | 10/2005 | Higashida et al. | |
| 7,844,324 B2 | 11/2010 | Saerkelae et al. | |
| 7,904,144 B2 | 3/2011 | Causevic et al. | |
| 7,962,204 B2 | 6/2011 | Suffin et al. | |
| 7,986,991 B2 | 7/2011 | Prichep | |
| 8,103,333 B2 | 1/2012 | Tran | |
| 8,108,036 B2 | 1/2012 | Tran | |
| 8,114,021 B2 | 2/2012 | Robertson et al. | |
| 8,147,419 B2 | 4/2012 | Krauss et al. | |
| 8,190,248 B2 | 5/2012 | Besio et al. | |
| 8,190,249 B1 | 5/2012 | Gharieb et al. | |
| 2003/0055355 A1 | 3/2003 | Viertio-Oja | |
| 2004/0078219 A1 | 4/2004 | Kaylor et al. | |
| 2004/0249249 A1 | 12/2004 | Lawson et al. | |
| 2005/0240087 A1 | 10/2005 | Keenan et al. | |
| 2005/0283053 A1 | 12/2005 | DeCharms | |
| 2006/0009697 A1 | 1/2006 | Banet et al. | |
| 2006/0063980 A1 | 3/2006 | Hwang et al. | |
| 2006/0173510 A1 | 8/2006 | Besio et al. | |
| 2007/0061735 A1 | 3/2007 | Hoffberg et al. | |
| 2007/0100246 A1 | 5/2007 | Hyde | |
| 2007/0150025 A1 | 6/2007 | DiLorenzo et al. | |
| 2007/0208263 A1 | 9/2007 | John et al. | |
| 2007/0219455 A1 | 9/2007 | Wong et al. | |
| 2008/0108908 A1 | 5/2008 | Maddess et al. | |
| 2008/0146890 A1 | 6/2008 | Leboeuf et al. | |
| 2008/0177197 A1 | 7/2008 | Lee et al. | |
| 2009/0018405 A1 | 1/2009 | Katsumura et al. | |
| 2009/0024050 A1 | 1/2009 | Jung et al. | |
| 2009/0062676 A1 | 3/2009 | Kruglikov et al. | |
| 2009/0214060 A1 | 8/2009 | Chuang et al. | |
| 2009/0247894 A1 | 10/2009 | Causevic | |
| 2009/0292180 A1 | 11/2009 | Mirow | |
| 2009/0318825 A1 | 12/2009 | Kilborn | |
| 2010/0010336 A1 | 1/2010 | Pettegrew et al. | |
| 2010/0010364 A1 | 1/2010 | Verbitskiy | |
| 2010/0022820 A1 | 1/2010 | Leuthardt et al. | |
| 2010/0022907 A1 | 1/2010 | Perez-Velazquez et al. | |
| 2010/0042011 A1 | 2/2010 | Doidge et al. | |
| 2010/0049004 A1 | 2/2010 | Edman et al. | |
| 2010/0169409 A1 | 7/2010 | Fallon et al. | |
| 2010/0286549 A1 | 11/2010 | John et al. | |

(Continued)

FOREIGN PATENT DOCUMENTS

WO    2010147913 A1    12/2010

OTHER PUBLICATIONS

Stam et al., Nonlinear Synchronization in EEG and Whole-Head MEG Recordings of Healthy Subjects, date unknown.

(Continued)

*Primary Examiner* — Eric S Dejong
(74) *Attorney, Agent, or Firm* — Jeffrey Schox; Ivan Wong

(57) ABSTRACT

A method and system for providing and aggregating bioelectrical signal data comprising: providing a stimulus configured to prompt an action in both a first user and a second user; at a first biosignal detector and a second biosignal detector, automatically collecting a first bioelectrical signal dataset from the first user as the first user performs the action and a second bioelectrical signal dataset from the second user as the second user performs the action; generating a first anonymized bioelectrical signal dataset from the first bioelectrical signal dataset and a second anonymized bioelectrical signal dataset from the second bioelectrical signal dataset; coupling the first and the second anonymized bioelectrical signal datasets with an action tag characterizing the action; and generating an analysis based upon the first the second anonymized bioelectrical signal datasets. An embodiment of the system comprises a biosignal detector and a processor configured to implement an embodiment of the method.

23 Claims, 6 Drawing Sheets

(56) References Cited

U.S. PATENT DOCUMENTS

| | | |
|---|---|---|
| 2011/0071364 A1 | 3/2011 | Kuo et al. |
| 2011/0087125 A1 | 4/2011 | Causevic |
| 2011/0184247 A1 | 7/2011 | Contant et al. |
| 2011/0245633 A1 | 10/2011 | Goldberg et al. |
| 2011/0270117 A1 | 11/2011 | Warwick et al. |

OTHER PUBLICATIONS

Park, et al. "Multiscale Entropy Analysis of EEG from Patients Under Different Pathological Conditions." Fractais 15, 399 (2007).

SYSTEM AND METHOD FOR PROVIDING AND AGGREGATING BIOSIGNALS AND ACTION DATA

CROSS-REFERENCE TO RELATED APPLICATIONS

This application claims the benefit of U.S. Provisional Application Ser. No. 61/652,040 filed 25 May 2012 and U.S. Provisional Application Ser. No. 61/679,044 filed 2 Aug. 2012, which are incorporated in their entirety herein by this reference.

TECHNICAL FIELD

This invention relates generally to the biosignals field, and more specifically to a new and useful system and method for providing and aggregating biosignal and action data in the biosignals field.

BACKGROUND

The general populace interacts with a wide variety of sensors on a daily basis, and vast amounts of data pertaining to individuals and entire groups of people is collected from these sensors. This data can be anchored in the physical realm, such as location data provided through a GPS sensor, caloric expenditure provided by an exercise machine, footstep count provided by an accelerometer-based step counter, or heart rate, body temperature, respiratory rate, or glucose level provided by a biometric sensor. This data can also be more abstract, such as interests as indicated by websites visited or needs as indicated by purchases made through an online store. This data can provide significant insight into market trends, needs, and interests of a particular demographic, and this data can even be used to target a user with particular physical and digital goods and services. However, contemporary sensors, data collection, and data analysis fail to capture cognitive, mental, and affective states of individuals and groups of people that can provide similar insight. Furthermore, contemporary data collection fails to efficiently locate, obtain, and aggregate biosignal data from multiple or selected individuals and make this data available for analysis. Thus, there is a need in the biosignals field for a new and useful system and method for providing and aggregating biosignal and action data.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1A:
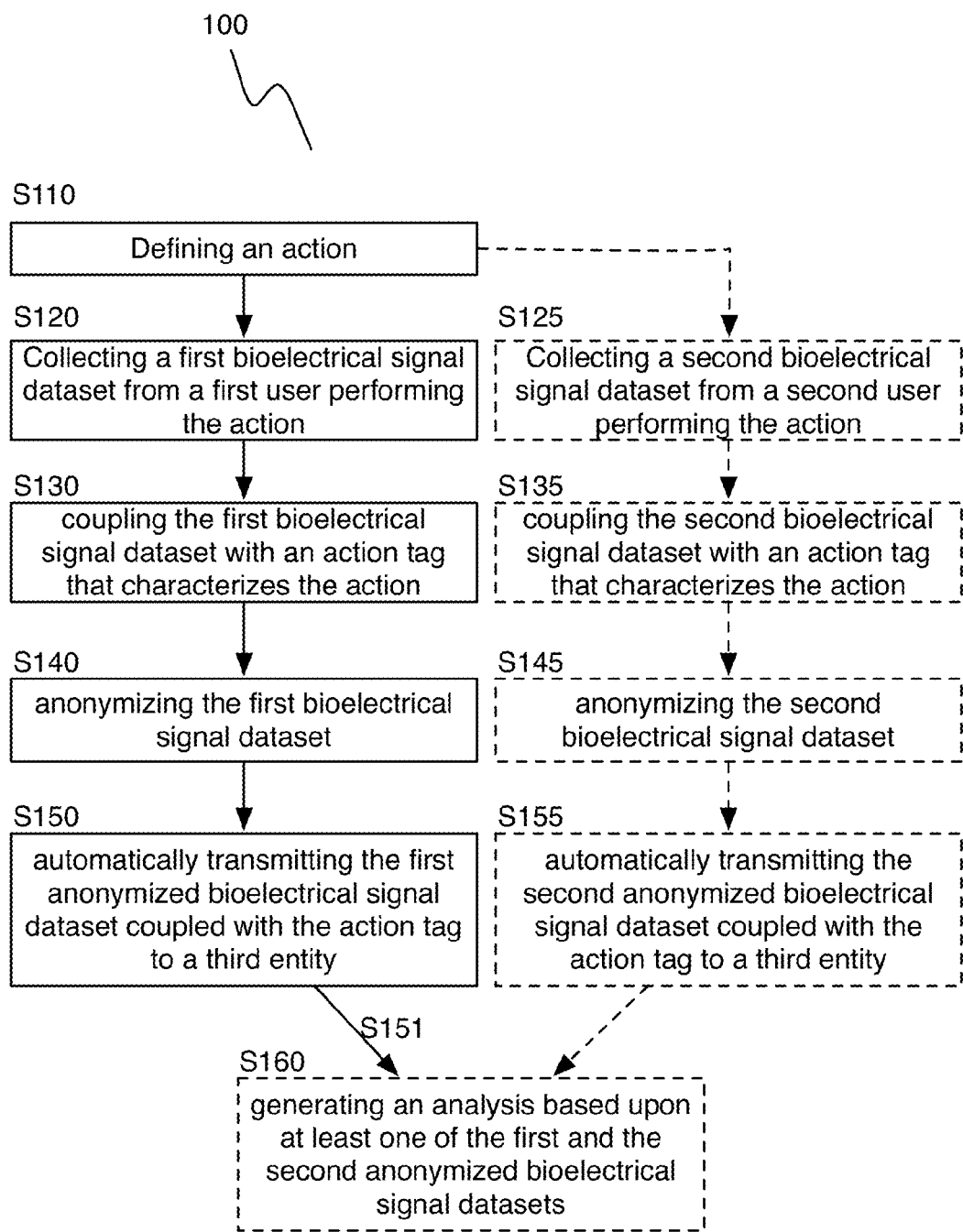
FIG. 1A is a flowchart representation of an embodiment of a method for providing and aggregating bioelectrical signal data.
Figure 1B:
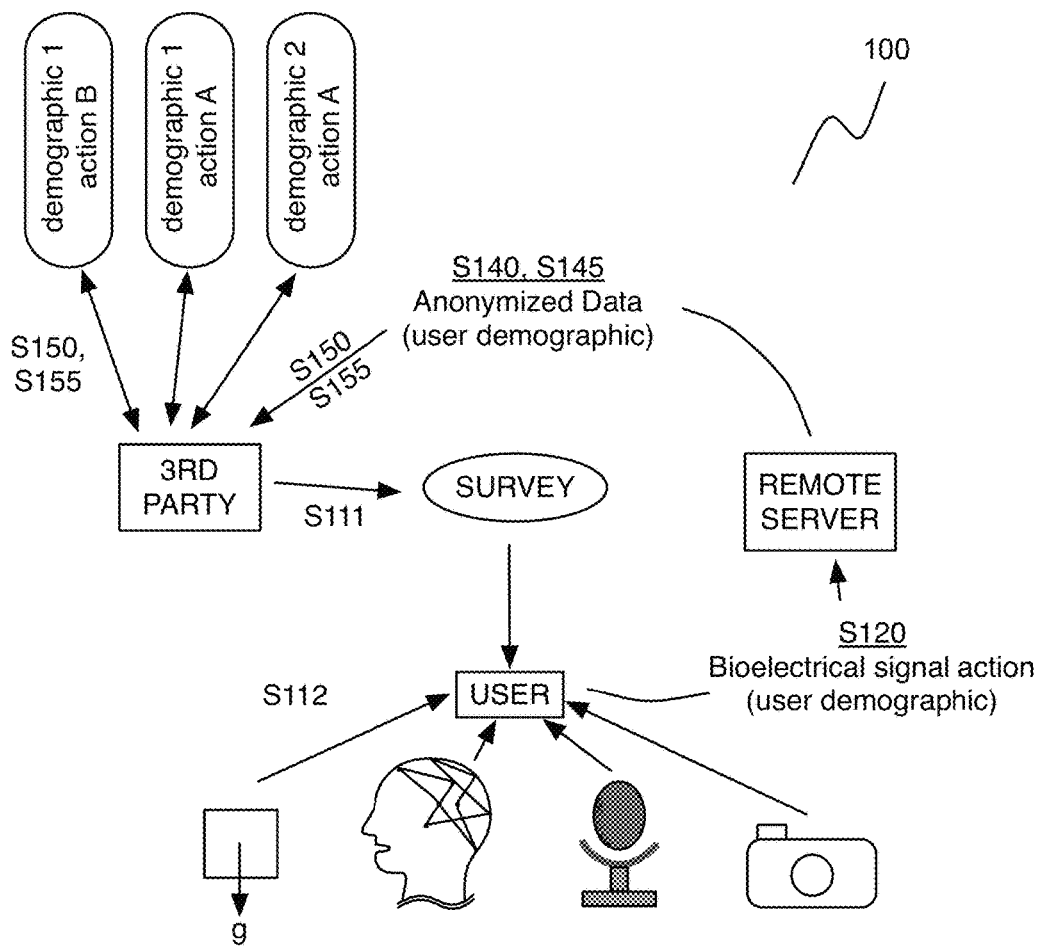
FIG. 1B is a schematic of an embodiment of a method for providing and aggregating bioelectrical signal data.

As shown in FIGS. 1A and 1B, an embodiment of a method 100 for providing and aggregating bioelectrical signal data comprises defining an action S110; collecting a first bioelectrical signal dataset from a first user performing the action S120; coupling the first bioelectrical signal dataset with an action tag that characterizes the action S130; anonymizing the first bioelectrical signal dataset S140; and automatically transmitting the first anonymized bioelectrical signal dataset coupled with the action tag to a third entity S150. The method 100 may further comprise collecting a second bioelectrical signal dataset from a second user performing the action S125; coupling the second bioelectrical signal dataset with the action tag S135; anonymizing the second bioelectrical signal dataset S145; automatically transmitting the second anonymized bioelectrical signal dataset coupled with the action tag to the third entity S155; and generating an analysis based upon at least one of the first and the second anonymized bioelectrical signal datasets S160.

The method 100 functions to facilitate collection of bioelectrical signals while a user engages in a particular action (or activity), to associate the bioelectrical signal data with the action by use of an action tag and other relevant user-based data, and to provide the bioelectrical signal data in anonymized form to a third entity (e.g., a remote server executing an analysis tool or a third party). The method 100 can further function to enable an analysis of a user's bioelectrical signal data to be performed relative to other data from the user, and/or to enable an analysis of a user's bioelectrical signal data to be performed relative to data from another user (or group of users). The analyses can also be performed on data collected at multiple time points and/or under different circumstances (e.g., actions or activities) from a single user or group of users. Thus, the method 100 may even be split into at least two sub-methods, comprising a first sub-method that functions to collect and tag bioelectrical signal data, and a second sub-method that functions to process and generate an analysis based upon collected bioelectrical signal data. In one application, the method 100 can be used to design user-response experiments by selecting a given demographic group, automatically collecting bioelectrical signal datasets from multiple users of the demographic group in parallel, and generating an analysis (e.g., using signal analysis, data mining, etc.) based upon the datasets in order to extract information relating the demographic group and a stimulus or action that produces a response within the demographic group.

The method 100 is preferably performed using an embodiment of a system 300 comprising a biosignal detector 300 and a processor 320 comprising a receiver 330, an anonymizer 340, a coupler 350, an analyzer 360, and a stimulus transmission module 370, as described in further detail below; however, the method 100 may be performed using any suitable system configured to collect and transmit bioelectrical signal data from a user.

Step S110 recites defining an action, and functions to enable coupling of an action performed by a user with a bioelectrical signal dataset collected from the user while the user performs the action. The action of Step S110 can further function to define a window (e.g., a window of time) for bioelectrical signal collection, wherein the window encompasses bioelectrical signals captured while a user or group of users engages in the action. Step S110 preferably includes defining at least one of an active and/or a passive action, but can additionally or alternatively include any other suitable action performed by a user. Examples of active actions include playing an instrument, driving a car, conversing, writing, reading, studying, eating, cooking, surfing the web, and exercising. Examples of passive actions include sleeping, resting, listening to music, and watching television. Other suitable actions performed by the user may comprise involuntary actions, such as evoked signals and reflex reactions, and may be characterized by reaction times.

Figure 2:
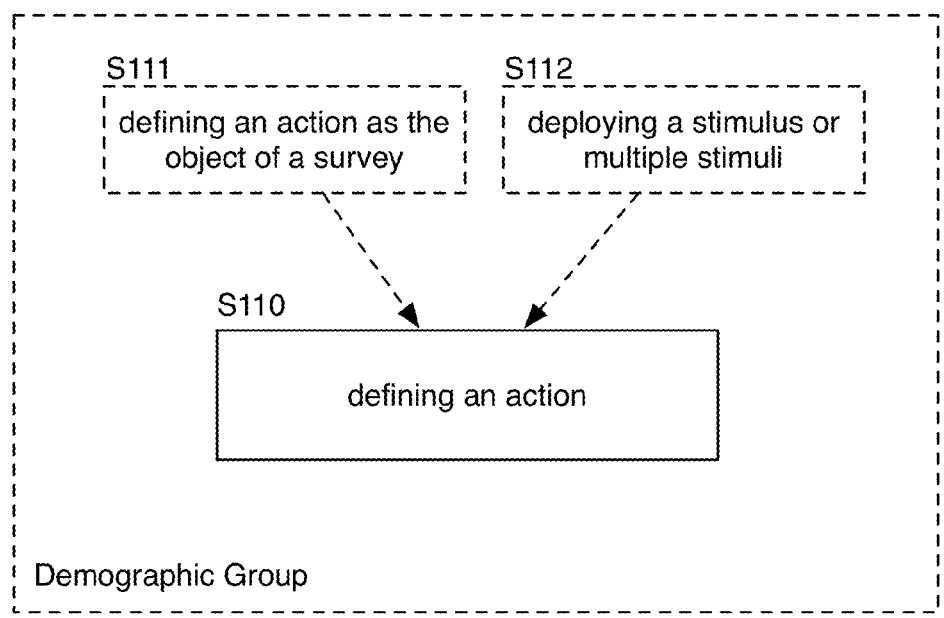
FIG. 2 is a flowchart representation of an embodiment of a portion of a method for providing and aggregating bioelectrical signal data.

As shown in FIG. 2, Step S110 can comprise defining an action as the object of a survey S111. Step S110 can further include limiting the survey to a particular demographic, characterized by a factor such as age, gender, dexterity (e.g., left- or right-handedness), education, occupation, mental or physical disorder or disability, location, hobby, interest, or any other characteristic or profile of a potential subject (i.e. the user). Thus, bioelectrical signals can be collected from users of a specific demographic while they perform a specific action or action(s), and the bioelectrical signal data can be analyzed accordingly to extract meaningful information in a controlled manner. Through Step S110, an entity (e.g., remote server executing an analysis tool, third party) can even define 'who' is surveyed 'when' performing 'what' action. Details of the survey can be defined through an application programming interface (API) hosted by a data storage module. Alternatively, defining an action may not comprise defining an action as the object of a survey, such that a user or other entity can define actions performed by the user, which are not included in a survey.

In variations of Step S110 comprising defining an action as the object of a survey, details of the survey (e.g., actions, demographic, user characteristics) can be provided to the user through a native application executing on a mobile or other electronic device or through a web browser, wherein the user is encouraged to complete the survey by wearing a biosignal detector and performing the action. Content related to, specifying, or describing actions, such as cognitive tasks, neuropyschological tests, advertisements, music content, video content, or evoked potential stimuli can also be provided to the user through such an application or web browser. The user can also be rewarded for completing the survey, such as with a monetary, physical, or digital prize, access to further EEG-supported features, free or discounted EEG analysis, or any other suitable reward.

Step S110 can further comprise providing a stimulus S112, which functions to generate or prompt a bioelectrical signal response (i.e., an action) in a user or group of users that can be collected and analyzed. The stimulus can be provided in any suitable manner, can be automatically or manually provided, and can be provided to multiple users (e.g., a demographic group) simultaneously or non-simultaneously. Furthermore, multiple stimuli can be provided, such that responses to combined stimuli and/or a sequence of stimuli can be later analyzed. The stimulus can be a notification, a command to perform an action, a haptic stimulus, a visual stimulus, an audio stimulus, or any other suitable stimulus. Furthermore, the stimulus can be time-locked (i.e., provided and/or presented within a specific time window characterized by an initiation time and a termination time) and/or presented at multiple timepoints to individual users. Additionally, provision of the stimulus/stimuli can be synchronized with user biosignal, biometric, and/or environment data substantially in real time, or upon detection of an event from user biosignal, biometric, and/or environment data. In one variation, the stimulus is provided using a mobile device of the user, or a set of mobile devices of a group of users, such that the stimulus can be provided at any point that a user or group of users is using the mobile device(s). In a first example, the stimulus is a command provided on a mobile device application that tells a user to go to a specific restaurant and eat a specific menu item. In a second example, the stimulus is a music piece that is automatically provided on a mobile device action, such that a reaction response to the music piece, captured in bioelectrical signal data collected from a user, can be analyzed. In a third example, the stimulus is a disturbing news story provided on a mobile device, such that a reaction response to the news story can be analyzed. In a fourth example, a combination of stimuli can be provided, such as a happy image rendered on a mobile device display followed by a sad music piece, such that reactions to combinations of stimuli can be later analyzed. In a fifth example with a combination of stimuli, a user or group of users can be presented with different music samples while exercising, such that responses to different types of music while exercising, captured in bioelectrical signal data, can be collected and analyzed. In a sixth example, the stimulus is automatically provided upon detection that a user is exercising, as determined from additional biosignal, biometric, and or environment data. Thus, Step S112 allows a stimulus or a combination of scriptable stimuli to be provided to a user or a group of users, which enables fully deployable automated experiments to be performed.

Step S120 recites collecting a first bioelectrical signal dataset from a first user performing the action, and functions to provide bioelectrical signal data that can be analyzed by another entity (e.g., remote server executing an analysis tool, third party) to extract meaningful information. Preferably, the bioelectrical signal data includes electroencephalograph (EEG) data, which can be reflective of cognitive, mental, and affective state of the user. However, the bioelectrical signal data can additionally or alternatively include any one of more of: data related to magnetoencephalography (MEG) impedance or galvanic skin response (GSR), electrocardiography (ECG), heart rate variability (HRV), electrooculography (EOG), and electromyelography (EMG). Furthermore, Step S120 can comprise collecting other biosignal data, including data related to cerebral blood flow (CBF), optical signals (e.g., eye movement, body movement), mechanical signals (e.g., mechanomyographs) chemical signals (e.g., blood oxygenation), acoustic signals, temperature, respiratory rate, and/or any other data obtained from or related to biological tissue or biological processes of the user, as well as the environment of the user. Additionally, the bioelectrical signal data preferably includes data acquired from multiple channels, wherein each channel is associated with a particular sensor arranged on a particular location or region of the user (e.g., head region, torso region). The bioelectrical signal data can alternatively comprise a single signal (e.g., from a single channel or as a composite of multiple channels), or a plurality of composite signals, each of which is a composite of multiple channels. The bioelectrical signal can also be a compressed, filtered, analyzed, or otherwise processed version of raw bioelectrical signals from one or more sensors. However, the bioelectrical signal data can be of any other suitable form or format.

Figure 3:
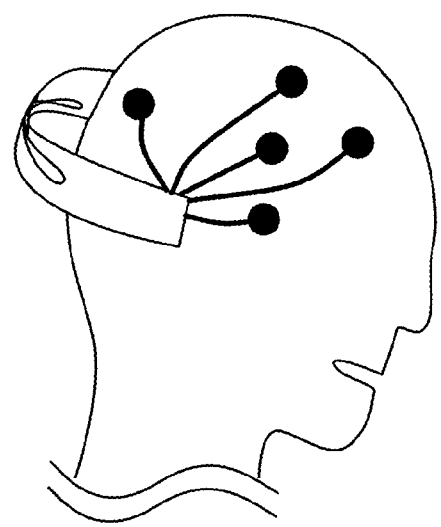
FIG. 3 depicts an embodiment of a biosignal detector.

In Step S120, collecting a first bioelectrical signal dataset preferably comprises collecting a first bioelectrical signal dataset at a biosignal detector that is worn by the first user while he/she performs the action defined in Step S110. In one variation, Step S120 is performed using a portable biosignal detector that can operate outside of a clinical (e.g., hospital) or research (e.g., laboratory) setting, such that the first user can be in a non-contrived environment as the bioelectrical signal dataset is collected. In another variation, Step S120 is performed using a biosignal detector operating within a clinical or research setting. In a specific example of Step S120, the first user wears a portable EEG device, an example of which is shown in FIG. 3, while performing a substantially normal, everyday activity, such as playing a sport, shopping, working, or studying. In the specific example, the bioelectrical signal data (i.e., EEG signal data) is therefore collected while the user is outside of a hospital, lab, or purely medical setting and substantially removed from medical/research staff.

Furthermore, in Step S120, the bioelectrical signal dataset can be collected as described above and stored locally prior to transmission in Step S150, or can be stored on a separate device in communication with the biosignal detector. In variations, the separate device can be a mobile electronic device, such as a smartphone, a tablet, a personal data assistant (PDA), a laptop, or a digital music player. In other variations, the separate device can be a non-mobile device, such as a desktop computer, a gaming console, or any other suitable device. The separate device in these variations is preferably Internet-capable (e.g., via a Wi-Fi, cellular, or Ethernet connection) such that the bioelectrical signal dataset can be subsequently transmitted to a data storage module, and can be accessed by a user or other entity; however, the bioelectrical signal dataset can be accessible in any other suitable manner. By accessing the bioelectrical signal dataset following recordation, the user or other entity can associate an action, activity, person, location, mood, weather, or other relevant personal or action-related information with the bioelectrical signal. In a specific example, this information is automatically captured through a smartphone device that stores a bioelectrical signal (e.g., EEG signal) locally, through a mobile application executing on the smartphone and in communication with the data storage module. In another specific example, the user provides any of the foregoing personal or action-related information (or subsets of information) through a web browser or application executing on a non-mobile electronic device and in communication with the data storage module or through another venue, media, or method.

Collecting a bioelectrical signal dataset in Step S120 can be performed after defining an action in Step S110 in a first variation, substantially simultaneously with defining an action in Step S110 in a second variation, or prior to defining an action in Step S110 in a third variation. In the first variation, an action may be defined in Step S110, after which a user performs the action while bioelectrical signal data is collected. In the second variation, an action may be detected, prompting substantially simultaneous collection of bioelectrical signal data and defining of the action. In the third variation, a bioelectrical signal dataset may be collected, followed by defining an action characterized within the bioelectrical signal dataset during post-processing. For example, a stored bioelectrical signal dataset can be mined for actions, demographics, or other related information associated with the bioelectrical signal dataset. Furthermore, collecting a bioelectrical signal dataset in Step S120 can be triggered manually or automatically, as described in the following variations.

In a first variation of Steps S110 and S120, bioelectrical signal collection is triggered manually. In a first example of the first variation, the user activates a biosignal detector after an action has been defined by, for example, depressing a 'record' button, setting a timer to begin recording, and/or providing any other input to activate the biosignal detector. In a second variation of Steps S110 and S120, collection of bioelectrical signal data is triggered automatically. In a first example of the second variation, an accelerometer integrated into the biosignal detector can sense accelerations of the first user, enabling anticipation of the action of the first user based upon an accelerometer signal (e.g., predominantly vertical accelerations and small forward accelerations with peaks occurring at a frequency of approximately 2 Hz indicate that the user is walking, triggering bioelectrical signal capture). In a second example of the second variation, a camera proximal to the user cooperates with a processor implementing machine vision to determine objects or people proximal to the user, wherein the processor determines the user to be reading when an image depicts an open book in front of the first user, triggering bioelectrical signal capture. In a third example of the second variation, a microphone coupled to the biosignal detector captures an audio signal proximal to the user, wherein a processor recognizes cheering in the audio signal and determines that the user is watching a sporting event, triggering bioelectrical signal capture. In a fourth example of the second variation, a digital calendar of the user is accessed, wherein events on the calendar, including dates, times, and event descriptions, indicate an anticipated action of the first user at a particular time, triggering bioelectrical signal capture at the particular time. In a fifth example of the second variation, a biometric sensor coupled to the user collects biometric data (e.g., heart rate data, blood oxygen level data, and respiratory rate data) of the first user, which is correlated to a particular action (e.g., by a processor), triggering bioelectrical signal capture. However, any other sensor coupled to, in communication with, or integrated into a biosignal detector or data storage module can function independently or in cooperation with any other sensor or processor to estimate an action of the first user to trigger bioelectrical signal capture. Through the foregoing examples or any other example of signal capture and analysis, an action of the user can be aligned with the action defined in Step S110 to automatically initiate bioelectrical signal capture in Step S120. However, the action of the user can be indicated or determined in any other way or used to initiate and/or terminate bioelectrical signal capture in any other way. For example, a camera may detect a closed book suggesting that the user has finished reading, which terminates bioelectrical signal collection. Furthermore, any of the foregoing sensors or any other sensor can also be used to generate an action tag that is coupled with the bioelectrical signal dataset in Step S130.

As described above in the variations and examples of Step S120, collecting the bioelectrical signal dataset preferably includes collecting bioelectrical signal data taken while the user performs the action; however, Step S120 may further include collecting a baseline bioelectrical signal dataset S122 and/or collecting a repeat bioelectrical signal dataset S123. Collecting a baseline bioelectrical signal dataset can comprise collecting bioelectrical signal data while the user is in a neutral state, and functions to generate a baseline dataset against which other bioelectrical signal data from a user can be normalized or compared. In a specific example of collecting a baseline bioelectrical signal dataset, a set of EEG data can be taken while the user is stationary with eyes closed for a period of time (e.g., thirty seconds) prior to collecting bioelectrical signal data while an action is being performed (e.g., between an action initiation time point and an action termination time point). However, the baseline bioelectrical signal dataset can be of any other suitable active or passive action of the user and the EEG signal can include any other relevant EEG data. Collecting a repeat bioelectrical signal dataset functions to allow multiple bioelectrical signal datasets from a user to be collected and analyzed. The repeat bioelectrical signal dataset(s) can be collected while a user repeats a specific action, such that multiple datasets characterizing a substantially identical action can be analyzed; however, the bioelectrical signal dataset can be collected while the user performs a different action than a previously performed action. In one example, the first bioelectrical signal dataset can be collected while the user is listening to music, and the repeat bioelectrical signal dataset can be collected while the user is playing an instrument, such that data for complementary actions can be compared. In another example, the first bioelectrical signal dataset can be collected while the user is exercising and the repeat bioelectrical signal dataset can be collected while the user is resting, such that data for "opposite" actions can be compared.

As shown in FIG. 1A, Step S130 recites coupling the first bioelectrical signal dataset with an action tag that characterizes the action, and functions to relate an instance of collected bioelectrical signal data with a performed action to facilitate subsequent analyses. In one variation of Step S130, the identifier of the action (the 'action tag') is provided by the user or other entity, such as in a manner described above, wherein the user indicates the action before, during, or after collection of the bioelectrical signal dataset. In this variation, the action tag is preferably received through a user interface accessible or executing on an electronic device, such as a smartphone, cellular phone, tablet, laptop computer, desktop computer, PDA, a personal music player, or any other suitable electronic device.

In another variation of Step S130, the action tag is automatically generated and coupled to the bioelectrical signal dataset. Accelerometer data, a static image or video feed, GPS data, a pedometer output, or any other sensor output recorded during performance of the action by the user can be analyzed to automatically generate the action tag and couple the action tag to the collected bioelectrical signal dataset. In one example, a processor coupled to a camera adjacent the user and implementing machine vision and machine learning techniques can isolate objects within the field of view of the camera to couple an associated action tag (e.g., an action tag related to cooking if the camera detects a pot, spoon, and stovetop adjacent the user) to the bioelectrical signal dataset. In another example, a personal and portable EEG device is coupled to an electronic device, either via a wired connection, a direct wireless connection (e.g., Bluetooth), or an indirect wireless connection (e.g., over Wi-Fi via a local or remote server). The electronic device in the example can be a desktop or laptop computer, a tablet, a smartphone, or a PDA enabling internet access through a web browser such that a browser plug-in or add-on can monitor user actions and interactions through the web browser. In the example, the browser plug-in or add-on can determine when the user is editing or reviewing a calendar, reading an email, checking bank balances, looking up recipes, shopping, chatting via an instant messenger, reviewing a class online, engaging a social network, or performing any other action through the web browser. Once the action is determined by the browser plug-in or add-on, an action tag can be generated and coupled to the bioelectrical signal dataset. In another version of the example, a native monitoring application executing (e.g., passively, in the background) on the electronic device can monitor user actions and interactions within other native applications accessed by the user through the electronic device. In the other version of the example, the native monitoring application can determine when the user is reviewing a calendar within a calendar application, reading an email within an email application, checking bank balances through a bank application, looking up a recipe within a food application, shopping via a retailer application, communicating via a messaging application, engaging a social network through a social network application, or performing any other action or interaction through a native application executing on the electronic device. Upon determination of the action, an action tag is generated and subsequently coupled to the collected bioelectrical signal dataset. In the foregoing examples, the plug-in, add-on, native monitoring application, etc. preferably generates the action tag automatically based upon the determined or estimated action or interaction of the user provided through the web browser or other native applications. Alternatively, the plug-in, add-on, native monitoring application, etc. can collect adequate information to enable a remote server to independently or cooperatively generate the action tag and couple the action tag to the set of bioelectrical signal data.

In Step S130, the bioelectrical signal dataset coupled with the action tag preferably comprises a media-rich file format in which the action tag is text-based and includes a timestamp for a specific time or time period spanning the bioelectrical signal dataset. Alternatively, the action tag can be a labeled bucket for bioelectrical signal data stored on or maintained by a data storage module, wherein the bioelectrical signal data of the user is placed in the bucket with other bioelectrical signal data from other users engaging in similar or identical actions. The action tag can also be distinct from the bioelectrical signal data, such as a text- or other media-rich file separate from the bioelectrical signal data. However, the action tag can be of any other suitable form. Furthermore, the bioelectrical signal data can also include personal or action-related information, such as a demographic of the user or the location and time of the action as determined automatically and/or provided by the user or other entity.

Step S140 recites anonymizing the first bioelectrical signal dataset, and functions to remove sensitive identifying information from the first bioelectrical signal dataset in a manner that allows analyses to be performed using the first bioelectrical signal dataset. Step S140 preferably strips substantially private information from the bioelectrical signal data associated with a user, such as the identity, email address, account number, billing address, or other personal information of the user. Alternatively, transfer of identifying information can be limited, or anonymization can be performed by another entity (e.g., remote server executing an analysis tool, third party), such as before analysis or manipulation of the bioelectrical signal data. Step S140 therefore preferably retains bioelectrical signal data collection and dissemination within the bounds of relevant privacy and security laws, such as those defined by the Health Insurance Portability and Accountability Act (HIPAA). In Step S140, anonymizing the first bioelectrical signal dataset can further comprise anonymizing the action tag, such that both the bioelectrical signal dataset and the action tag(s) are anonymized. Preferably, the action tag is not anonymized with the bioelectrical signal dataset to facilitate experimentation; however, anonymizing the action tag can be performed depending upon the preference of the user and/or other entity.

Step S150 recites automatically transmitting the first anonymized bioelectrical signal dataset coupled with the action tag to a third entity, and functions to provide data with an associated action tag to a third entity (e.g., remote server executing an analysis tool, third party) for analysis. The anonymized bioelectrical signal dataset and action tag can be provided in a bucket of bioelectrical signal datasets and action tags from multiple users, wherein the bucket identifies a certain demographic or action requested in the survey as defined in a variation of Step S110. The bioelectrical signal dataset transmitted to the third entity in Step S150 can also be an original, composite, cropped, filtered, compressed, analyzed, or otherwise manipulated version of raw signals from the sensors of a biosignal detector; can include baseline and/or repeat bioelectrical signal data; and/or can include any other relevant user demographic or characteristic data. Furthermore, the bioelectrical signal dataset and action tag can be transmitted in any suitable fashion (e.g., transmitted via a data storage module, transmitted using a wireless connection, transmitted using a wired connection). Additionally, the bioelectrical signal dataset(s) can be transmitted substantially in real time, such as during recordation of the signal, or once bioelectrical signal capture is complete. Transmission can also be delayed until released or verified by the user, until released by a parent, teacher, legal guardian, or other entity, or until requisite personal or action-related information is provided for the bioelectrical signal dataset(s).

In some variations, Step S150 may further comprise receiving a bioelectrical signal dataset identified with the first user and associated with the action S151. In Step S151, a third party or other entity preferably receives the bioelectrical signal dataset from a data storage module; however, the third party of other entity can receive the bioelectrical signal dataset and/or action tag in any suitable manner. Multiple bioelectrical signal datasets coupled with action tags aligned with a given demographic, action, etc. can also be received by the third party or other entity in Step S150 to further facilitate analyses based upon data from a single user or multiple users, performing similar actions or different actions.

As shown in FIG. 1A, the method 100 may further comprise collecting a second bioelectrical signal dataset from a second user performing the action S125; coupling the second bioelectrical signal dataset with the action tag S135; anonymizing the second bioelectrical signal dataset S145; automatically transmitting the second anonymized bioelectrical signal dataset coupled with the action tag to the third entity S155. Individually, Steps S125, S135, S145, and S155 have similar functions to their counterpart Steps S120, S130, S140, and S150, respectively, as described above; however, Steps S125, S135, S145, and S155 collectively function to enable analyses to be performed based upon bioelectrical signal datasets collected from a first user and a second user. In some variations, however, collecting bioelectrical signal datasets in Steps S120 and S125 may be performed at a single biosignal detector, or at a first biosignal detector and a second biosignal detector. Steps S125, S135, S145, and S155 are thus analogous to the embodiments, variations, and examples of Steps S120, S130, S140, and S150, respectively as described above.

Figure 5:
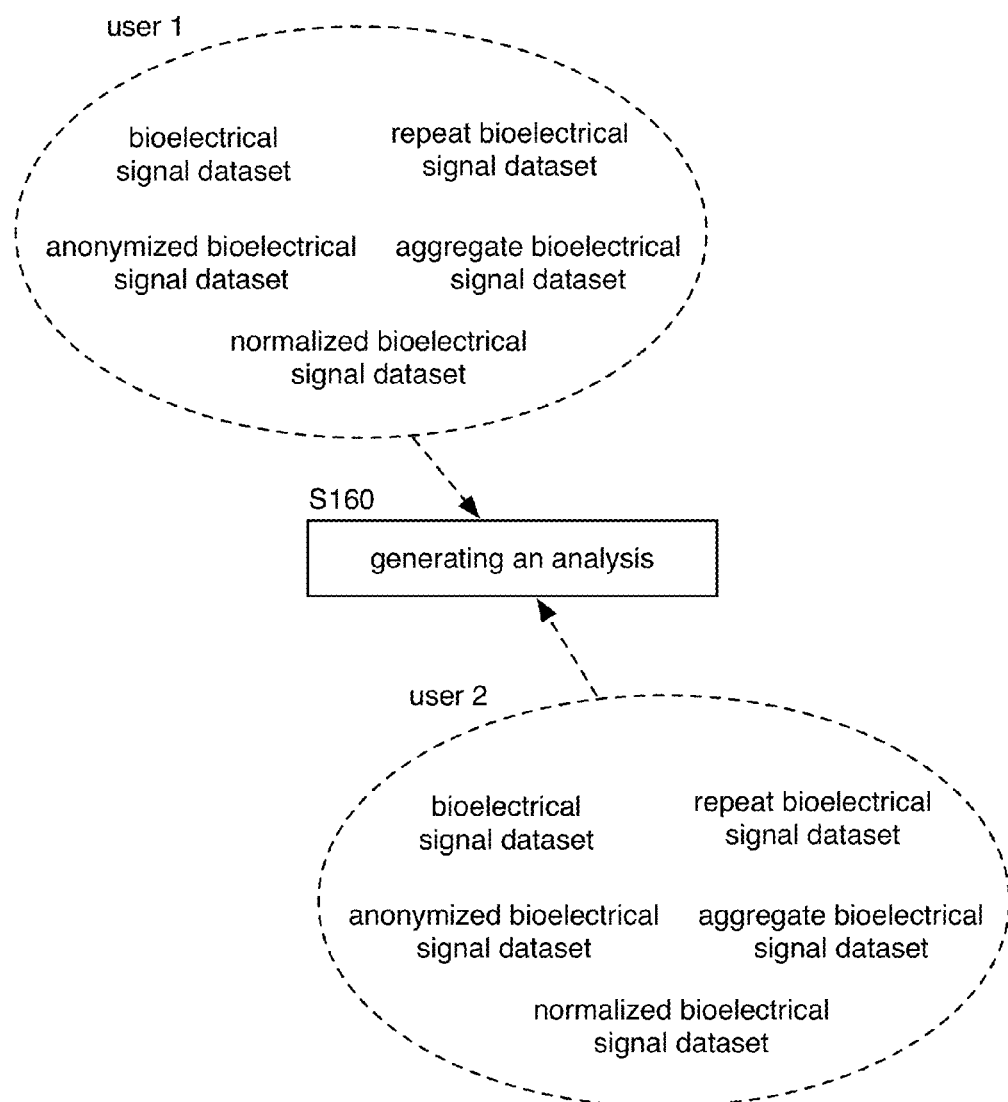
FIG. 5 is a flowchart representation of an embodiment of a portion of a method for providing and aggregating bioelectrical signal data.

As shown in FIGS. 1A and 5, the method may further comprise Step S160, which recites generating an analysis based upon at least one of the first and the second anonymized bioelectrical signal datasets. Step S160 functions to extract information from bioelectrical signals collected from a single user or a multiple users, by providing an analysis based upon the bioelectrical signal dataset(s), the baseline bioelectrical signal dataset(s), and/or the repeat bioelectrical signal dataset(s). The analysis can be further used to adjust the stimulus/stimuli in variations wherein the method 100 comprises iterations between collecting bioelectrical signal data and providing stimuli configured to prompt a user action. The analysis can also be used to provide information about a demographic group comprising the first user and the second user, or to control an environment of the first user and/or the second user. The analysis generated in Step S160 can be implemented on a remote server or any other suitable module configured to generate the analysis. Furthermore, the analysis can be generated using signal analysis, data mining operations, and/or any other suitable method of analyzing bioelectrical signal data. In a first variation, an analysis is generated based upon a bioelectrical signal dataset and at least one of a baseline bioelectrical signal dataset and a repeat bioelectrical signal dataset from a first user. In a second variation, an analysis is generated based upon at least one of a bioelectrical signal dataset, a baseline bioelectrical signal dataset, and a repeat bioelectrical signal dataset from a first user, and at least one of a bioelectrical signal dataset, a baseline bioelectrical signal dataset, and a repeat bioelectrical signal dataset from a second user.

Figure 4:
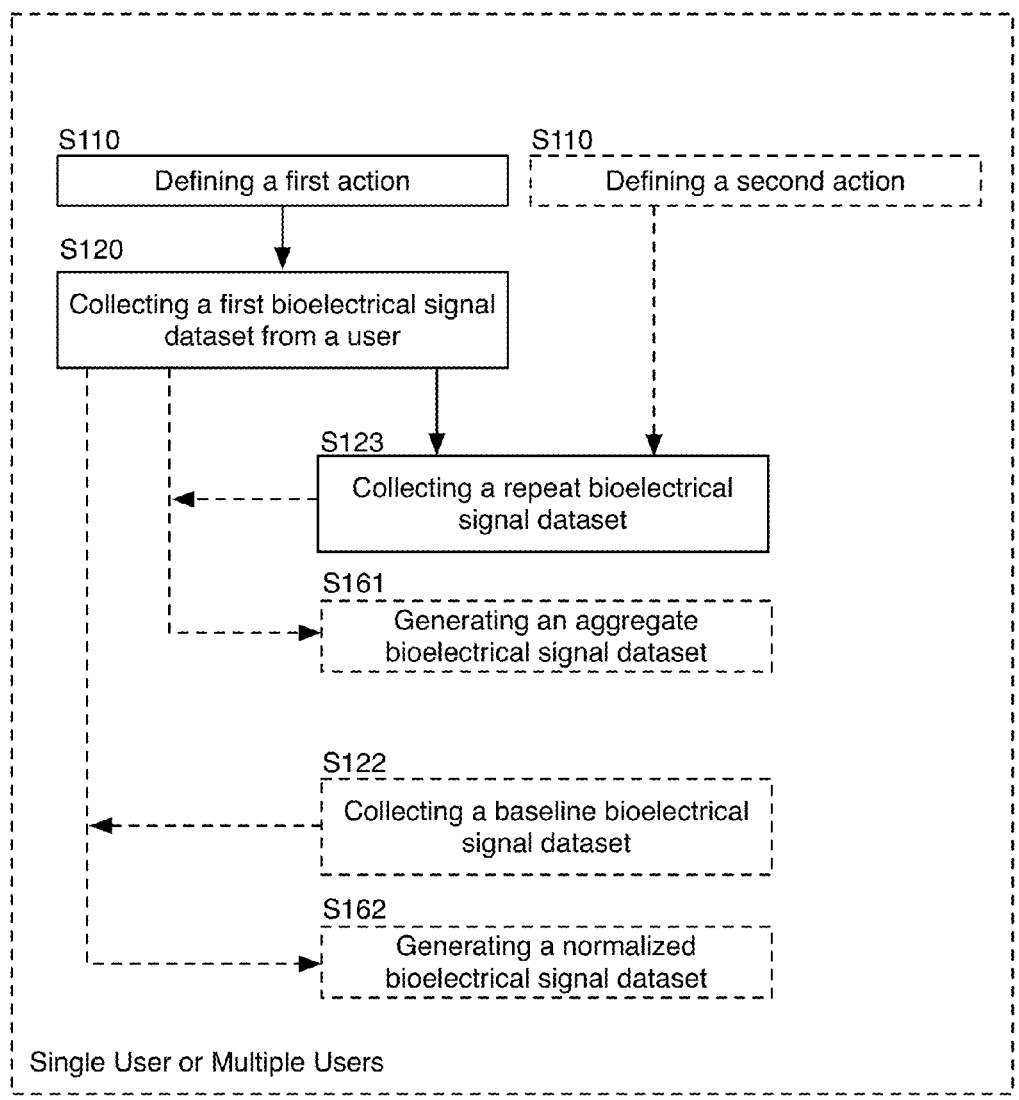
FIG. 4 is a flowchart representation of an embodiment of a portion of a method for providing and aggregating bioelectrical signal data.

In the first variation of Step S160, an analysis is generated based upon bioelectrical signal data collected and transmitted from a single user. In an example of the first variation of Step S160, a bioelectrical signal dataset and at least one repeat bioelectrical signal dataset coupled with identical action tags (i.e., collected from the first user upon repeat performances of an action) can be combined to produce an aggregate bioelectrical signal dataset S161, as shown in FIG. 4. The aggregate bioelectrical signal dataset can then be processed to generate an analysis of a user's bioelectrical signal response based upon multiple datasets collected during multiple performances of a specific action (e.g., an action in response to a stimulus provided to the user, or an action defined as an object of a survey). In another example of the first variation, a bioelectrical signal dataset coupled with a first action tag and at least one repeat bioelectrical signal dataset coupled with a second action tag can be used to generate an analysis comparing bioelectrical signal data collected from a user while the user performs different actions (e.g., complementary or "opposite" actions). In another example of the first variation, at least one bioelectrical signal dataset and a baseline bioelectrical signal dataset can be used to generate an analysis involving a normalization of bioelectrical signal data to the baseline bioelectrical signal dataset. In this example, Step S160 can comprise generating a normalized bioelectrical signal dataset S162 for the user. In another example, bioelectrical signal data of the user can be compared against past bioelectrical signal data of the same user (e.g., collected at earlier time points) to track trends unique to the user or to guide the user through behavior changes to improve brain function. The first variation of Step S160 can, however, comprise any suitable version or combination of the described examples.

In the second variation of Step S160, an analysis is generated based upon bioelectrical signal data collected and transmitted from a first user and at least a second user. In an example of the second variation of Step S160, bioelectrical signal datasets (e.g., a bioelectrical signal dataset, an aggregate bioelectrical signal dataset, and/or a normalized bioelectrical signal dataset) from a first user and a second user are used to generate an analysis comparing bioelectrical signal data of the first user with bioelectrical signal data of at least one other user and associated with the same or similar action tag. In this example, the bioelectrical signal data of the user and at least one other user can be results of the same survey defined by a third entity in a variation of Step S110, or can be responses to a defined stimulus or combination of stimuli provided to the users in another variation of Step S110. In this example, the analysis can comprise a comparison of data from the users to indicate a trend across a population or demographic (e.g., effect of drawing faces on a population of autistic children, effect of music samples on a population of musicians). In another example of the second variation, bioelectrical signal datasets (e.g., a bioelectrical signal dataset, an aggregate bioelectrical signal dataset, and/or a normalized bioelectrical signal dataset) from a first user and a second user are used to generate an analysis comparing bioelectrical signal data of the first user with bioelectrical signal data of at least one other user and associated with the different action tags. In this example, the analysis can comprise a comparison of data from the users to indicate differences within subpopulations of a demographic when performing different actions (e.g., different responses to audio learning stimuli and visual learning stimuli in toddlers, responses to different therapy regimens in psychiatric patients). In other examples of the second variation, bioelectrical signal data of the user can be compared with trends in bioelectrical signal data from other users to estimate a characteristic of the user (e.g., as a diagnostic tool), to tailor an experience for the user, or to compare brain activity of the user to that of other users, such as when performing similar or dissimilar activities. Additionally, bioelectrical signal data of a first user can be aggregated with bioelectrical signal data of at least one other user, which can function to reduce outlier effects in the bioelectrical signal datasets and/or define population norms.

Again, Step S160 can comprise any variation or combination of the above described variations and examples, and can be extrapolated beyond the above variations to more than two users to generate analyses based upon groups of users (e.g., of a demographic or study group). Furthermore, Step S160 can comprise aggregation of non-bioelectrical biosignal data (e.g., data related to biological tissue or biological processes of the user, data related to the environment of a user or users) with bioelectrical signal data to generate the analysis in Step S160. The analysis can additionally or alternatively be generated according to any suitable combination of the embodiments, variations, and examples described above, using independent components analysis, or using any suitable method, such as those described in U.S. Pat. Pub. No. 2013/0035579, entitled "Methods for Modeling Neurological Development and Diagnosing a Neurological Impairment of a Patient", which is incorporated herein in its entirety by this reference. The method can also further comprise storing the analysis S165, which can facilitate other applications of the method 100, such as transmission of an analysis or further processing of a stored analysis.

The method 100 described above can have a variety of applications, a few of which are described as exemplary applications below.

1.1 Exemplary Applications of the Method

In one specific application of the method 100, the user is one of a group of volunteers, each with a portable biosignal detector configured to collect and transmit EEG data. The volunteers are recruited anonymously from a specific demographic group, and a stimulus or set of stimuli (e.g., audio stimuli, visual stimuli, haptic stimuli) is automatically provided to the volunteers substantially in real time (e.g., using an experimental tool, using a smartphone) while EEG data is automatically collected from each user in the group of volunteers. In this application, the action comprises responses to the stimulus/stimuli, and action tags associated with the responses are coupled with the EEG data collected from each user. The collected EEG data is anonymized and automatically transmitted, with the associated action tags and time stamps, to a central server for analysis. After transmission, the datasets are analyzed at the remote server to extract information relating the responses of the user and the specific demographic group to the provided stimulus/stimuli. In variations of this application, the provided stimulus/stimuli can be synchronized with biometric and/or environmental data (e.g., using video or audio of the user(s) and/or user environment(s)) acquired from each user in the group of volunteers, and self-reporting surveys can be transmitted with the collected EEG datasets to provide a greater pool of data for analysis. Furthermore, the application can comprise providing access to additional data from the group of volunteers and/or the general population, in order to provide reference against the collected data (e.g., to generate baseline data or population norms).

In another specific application of the method 100 an action is automatically defined via a plug-in, add-on, native monitoring application, etc. executing or accessible on an electronic device engaged by the user, and an EEG signal and action tag of the user are used to advise the user. Advice is provided to the user through the electronic device currently engaged by the user, such as through a pop-up message or by enabling or disabling certain features, functions websites, or other native applications accessible on or through the electronic device, in order to increase the user's productivity. In this application, trends in user productivity are linked to certain actions via the action tags charted with user EEG signals. Over time, certain stimuli (e.g., shopping website, a sports stats website, and a gaming website accessed through a web browser) that distract the user are detected from an analysis of the EEG data and the add-on or plug-in for the web browser thus automatically blocks access these sites. In another variation of this application, trends in user productivity are linked to certain open native applications via the action tags charted with user EEG signals. Over time, certain distractive applications are isolated, such as a daily deal application, a video-sharing application, and a social network application, and the native monitoring application generates a confirmation pop-up message when the user selects a distractive application, wherein the user is reminded of the distracting effect of the application and must click through the pop-up message to access the distractive application. However, the plug-in, add-on, native monitoring application, etc. executing or accessible on an electronic device engaged by the user can function in any other suitable way to implement the user EEG data and action tags to generate any other suggestion, advice, or interaction for the user.

In another specific application of method 100, compilation of EEG signals according to action tags and/or a demographic is used to track responses to a stimulus across the a population of the demographic. In a variation of this application, an analysis generated by the method 100 can be used to generate, manage, and/or modify advertising or marketing campaigns. In this variation of the application, the defined action can comprise viewing an advertisement (e.g., the advertisement is a provided stimulus), and EEG-based trend analyses can indicate which part of the brain is stimulated, when viewing the advertisement, for a user who eventually purchases the advertised product in comparison to a user who does not purchase the product. The EEG-based trend analyses can also indicate if user interest in the advertisement is fading over time, as suggested by decreased brain activity when viewing the advertisement, or if users enjoy, are satisfied with, or dislike the advertisement, as suggested by activation of specific brain regions. The EEG data can alternatively be used to generate content in an advertisement (i.e., adjusting the stimulus), such as by tracking habits of users engaging in the activity and determining positive reinforcement mechanisms for various users, wherein advertisements are designed to elicit similar brain activity to incite a purchase by the user. Reinforcement mechanisms taught by analysis of EEG data and trends in brain activity can thus be incorporated into an advertisement or marketing platform for a particular product or service.

In another specific application, the method 100 is used to conduct market research, in order to determine a need for a product or to develop a product. In this application, the defined action comprises interacting with a product. In this application, trends in EEG data across a population can indicate a level of satisfaction with a particular experience or product, such as revealed by reduced activity in one region of the brain associated with emotion (e.g., decreased in amygdala activity) and increased activity in another part of the brain associated with reasoning (e.g., increased prefrontal lobe activity). In one variation of this application, a survey defined in a variation of Step S110 can require a group of users to record EEG signals while engaging with a product or service and to then provide text-based responses to the product. Activity in certain parts of the brain across the population of users can then be associated with particular feelings or emotions, such as satisfaction, interest, memory, reasoning, or frustration. Products or service can then be created or modified to evoke activity in particular or focused portions of the brain, such as those portions indicative of a desired reaction to the product or service.

In yet another specific application of the method 100, the user is a student in a classroom, and the group of users comprises a population of students in the classroom. In this application, the defined action can comprise operating within the classroom, attending a lecture, performing an assignment, or any other suitable classroom-related action. EEG data for a class of students is analyzed to ascertain trends in brain activity in the class, wherein the trends are used to suggest changes in teaching style for all or a portion of the class or to suggest grouping of certain students according to similarities in responses to a stimulus, such as a lessons on a particular subject such as a math or geography. Trends in EEG data within the class can also indicate which subset of students are or are not grasping a particular subject or skill, the rate of learning in a subset of students, interests of a subset of students, learning disabilities in a subset of students, or any other relevant information, metric, or characteristic of students in the classroom. This application of the method 100 can therefore be implemented in an educational environment to improve student learning, to tailor content and teaching style for a subset of students, and/or to improve student-teacher interactions. Furthermore, in this application the population can alternatively be a group of students participating in a seminar or online class, rather than in a classroom.

In yet another specific application of the method 100, the user is part of a group of users undertaking a training activity such as an aptitude test or skilled physical movement. In this application the defined action comprises undertaking the training activity. EEG data of individuals in the group is analyzed to isolate a trend in brain activity within the group, wherein the trend suggests changes to the method of teaching or performing the activity for all or a portion of the group. In this application, the trend can further suggest grouping certain users according to similar responses to a stimulus, such as presentation of a question on an aptitude test with various questions types or difficulty levels. This application of the method 100 can therefore be implemented in a training environment to improve performance and/or to tailor a physical, cognitive, mental, or emotional approach to teaching or performing an activity for the user or a subset of users in a group.

In yet another specific application of the method 100, the user is an employee of a company, and the group of users comprises other employees at the company experiencing the work environment at the company. In this application, the defined action comprises operating within the work environment. Trends in brain activity within the work environment, as suggested by available EEG data, are used to suggest changes to the work environment, such as lighting, temperature regulation, arrangement of work spaces, work load, work flow, interactions between employees, employee habits, or any other relevant work-related information. This application of the method 100 can therefore be implemented in a work environment to increase employee efficiency, comfort, satisfaction, and throughput.

In yet another specific application of the method 100, the user is a member of a population receiving a particular medication or medical treatment and the action defined in a variation of Step S110 comprises at least one of consuming the medication and receiving the treatment. Emotional, mental, and even physical response to the medication or treatment can be tracked across the population through collected EEG data. In this application, the EEG data can indicate changes in pain levels, presentation of symptoms, side effects (e.g., drowsiness), changes in coordination, addiction or abuse risk, or any other relevant metric or characteristic of the medication or treatment. In this example, EEG data of each user prior to receiving the medication or treatment can also provide a baseline against which post-medication or -treatment changes are measured. The effectiveness of a particular medication can therefore be quantitatively or qualitatively ascertained via analysis of EEG data across a population consuming a medication.

In another specific application of the method 100, compilation of EEG signals according to action tags and/or demographics across multiple other users over time is compared against a stimulus response of the user, which provides insight into characteristics of the user. Learning habits and trends of the user can be compared against those of a greater population to suggest changes in how the user attempts to learn a particular material. For example, a user that is a student demonstrating subpar retention of new theoretical engineering material, as compared to peers, can be urged to engage in hands-on (e.g., in-lab) experiments or activities to reinforce theoretical material based upon a generated analysis from the user's EEG data. In this example, lower-than average retention of new material by the user can be indicated by reduced brain activity in a certain part of the brain as compared to a peer when engaging with the material. A learning or mental disability in the user can also be ascertained by comparing EEG data of the user with EEG data of other users, including those with and/or without learning or mental disabilities. Interest in educational material or work material, engagement in certain activities, progress in mastering a particular concept or skill, or any other quality or characteristic of the user can also be determined through this application of the method 100, and any other accompanying suggestion can be made based upon a comparison of the EEG data of the user with EEG data of at least one other user.

As a person skilled in the field of biosignals will recognize from the previous detailed description and from the figures and claims, modifications and changes can be made to the embodiments, variations, examples, and specific applications of the method described above without departing from the scope of the method 100.

2. System

Figure 6:
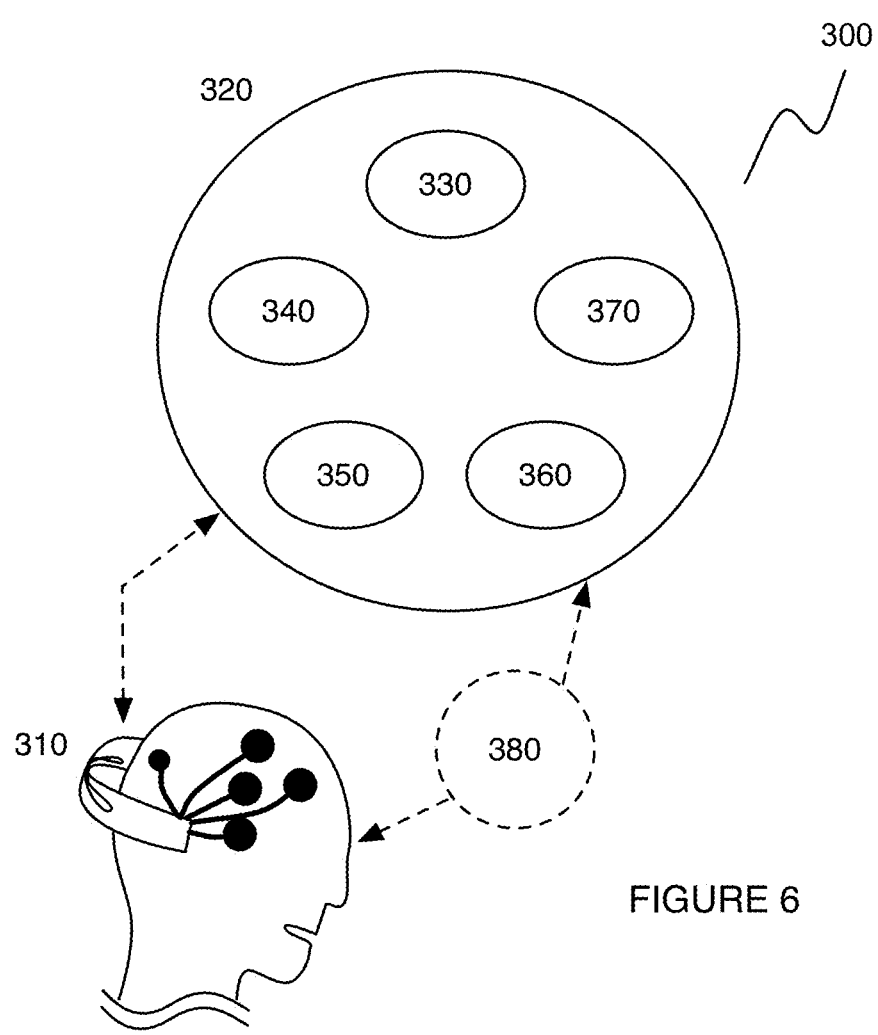
FIG. 6 is a schematic of an embodiment of a system for providing and aggregating bioelectrical signal data.

As shown in FIG. 6, an embodiment of a system 300 for providing and aggregating bioelectrical signal data comprises a biosignal detector 310 and a processor 320 comprising a receiver 330, an anonymizer 340, a coupler 350, an analyzer 360, and a stimulus transmission module 370. The system 300 can further comprise a data storage module 380. The system 300 functions to facilitate collection of bioelectrical signal data while a user engages in a particular action (or activity), to associate the bioelectrical signal data with the action by use of an action tag and other relevant user-based data, and to provide the bioelectrical signal data in anonymized form to a third entity (e.g., a remote server executing an analysis tool or a third party). The system 300 preferably enables a variation of the method 100 described above, but can alternatively facilitate performance of any suitable method involving collection and analysis of bioelectrical signal data.

The biosignal detector 310 functions to collect bioelectrical signal data from a user. The biosignal detector 310 preferably comprises a bioelectrical signal sensor system, wherein the sensor system comprises a plurality of sensors, each sensor providing at least one channel for bioelectrical signal capture. The plurality of sensors can be placed at specific locations on the user, in order to capture bioelectrical signal data from multiple regions of the user. Furthermore, the sensor locations can be adjustable, such that the biosignal detector 310 is tailorable to each user's unique anatomy. Alternatively, the sensor system can comprise a single bioelectrical signal sensor configured to capture signals from a single location. In one example, the biosignal detector can be a personal EEG device, such as the Emotiv EPOC neuroheadset, which is shown in FIG. 3. EEG devices are taught in the U.S. Patent Publication Nos. 2007/0066914 (Emotiv) and 2007/0173733 (Emotiv), which are also incorporated in their entirety by this reference.

The biosignal detector 310 can also comprise or be coupled to additional sensor systems configured to capture data related to other biological processes of the user and/or the environment of the user. As such, the biosignal detector 310 can comprise optical sensors to receive visual information about the user's environment, GPS elements to receive location information relevant of the user, audio sensors to receive audio information about the user's environment, temperature sensors, sensors to detect MEG impedance or galvanic skin response (GSR), sensors to measure respiratory rate, and/or any other suitable sensor. Furthermore, the system can comprise multiple biosignal detectors, each paired with a given user, such that bioelectrical signal data can be simultaneously collected from more than one user.

The processor 320 comprises a receiver 330, an anonymizer 340, a coupler 350, an analyzer 360, and a stimulus transmission module 370, and functions to receive and process bioelectrical signal data, biosignal data, and/or any other suitable data from the user or group of users. As such, the processor 320 can comprise a remote server configured to perform the functions of at least one of the receiver 330, the anonymizer 340, the coupler 350, the analyzer 360, and the stimulus transmission module 370. In this embodiment, the remote server can execute analysis tools to facilitate processing, analysis, storage, and/or transmission of data; however, the processor 320 can comprise any other suitable element or combinations of elements.

The receiver 330 functions to receive bioelectrical signal datasets from a single user or multiple users. The receiver 330 preferably comprises a wireless connection to a biosignal detector (or other suitable element for data transfer); however, the receiver 330 can alternatively comprise a wired connection. In wireless variations, the receiver 330 can implement wireless communications, including Bluetooth, 3G, 4G, radio, or Wi-Fi communication. In these variations, data and/or signals are preferably encrypted before being received by the receiver 330. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

The anonymizer 340 functions to remove sensitive identifying information from bioelectrical signal datasets. To anonymize data, the anonymizer 340 can comprise a data filter or any other suitable element that removes private and/or identifying information from a dataset. As such, the anonymizer 340 preferably strips substantially private information from the bioelectrical signal data associated with a user, such as the identity, email address, account number, billing address, or other personal information of the user. The anonymizer 340 therefore retains bioelectrical signal data collection and dissemination within the bounds of relevant privacy and security laws, such as those defined by the Health Insurance Portability and Accountability Act (HIPAA).

The coupler 350 functions to link a given dataset collected from a user to an action tag associated with an action performed by the user. As such, the coupler can be implemented in a software module that parses a bioelectrical signal dataset for identifiers of a given action performed by the user and/or that receives information related detection of the action along with collection of bioelectrical signal data. The coupler 350 can, however, comprise any suitable element configured to link a dataset with an action tag.

The analyzer 360 functions to generate an analysis of transmitted bioelectrical signal data and any other biosignal, biometric, and/or environment data. The analyzer 360 preferably implements signal analysis techniques and data mining algorithms; however, the analyzer 360 can additionally or alternatively implement any suitable methods or algorithms for processing bioelectrical signal data. In a first variation, the analyzer 360 is configured to generate an analysis based upon a bioelectrical signal dataset and at least one of a baseline bioelectrical signal dataset and a repeat bioelectrical signal dataset from a first user. In a second variation, the analyzer 360 is configured to generate an analysis based upon at least one of a bioelectrical signal dataset, a baseline bioelectrical signal dataset, and a repeat bioelectrical signal dataset from a first user, and at least one of a bioelectrical signal dataset, a baseline bioelectrical signal dataset, and a repeat bioelectrical signal dataset from a second user.

The stimulus transmission module 370 functions to facilitate provision of a stimulus or combination of stimuli to a user, in order to stimulate a user response that comprises an action performed by the user. As such, the stimulus transmission module 370 can comprise an alert system that provides a notification to the user, a module that gives a command to the user instructing the user to perform an action, a haptics system configured to provide haptic stimulus, a display configured to render a visual stimulus, an audio system configured to provide an audio stimulus, and/or any other suitable stimulus transmission system. Preferably, the stimulus transmission module 370 comprises a controller that controls delivery of the stimulus/stimuli, with regard to timing, frequency, and/or duration. In one variation, at least a portion of the stimulus transmission module 370 is implemented on a mobile device of the user, or a set of mobile devices of a group of users, such that a given stimulus or combination of stimuli can be provided at any point that a user or group of users is using the mobile device(s). The system can, however, comprise any other suitable stimulus transmission elements to provide a stimulus to one or more users.

The system 300 can further comprise a data storage module 380, which functions to receive and store collected data and/or analyses. Preferably, bioelectrical signal data and other enriching data is transmitted to and maintained by the data storage module 380. Furthermore, the data storage module 380 is preferably remote from the biosignal detector 310. In some variations, the data storage module 380 can be a remote server configured to host or communicate with an application programming interface (API), wherein the API allows accessing and manipulation of data stored in the data storage module 380. In one example, the biosignal detector 310 can be Internet-capable and transmit data directly to the data storage module 380, or the biosignal detector 310 can communicate via a wireless or wired connection with a local electronic device, such as a smartphone or tablet, that transmits the data to the data storage module 380. Alternatively, bioelectrical signal data and additional enriching data can be maintained by a data storage module 380 that operates, at least in part, on an electronic device that is local to the user and configured to communicate with the biosignal detector 310. In any of the foregoing variations, the bioelectrical signal data and enriching data is preferably accessible by the user, from the data storage module 380, to view, augment, or update any portion of the data. Data can be transmitted to the data storage module 380 substantially in real time, such as during recordation of the signal, or once the data collection is completed, verified, or released by the user.

The method 100 and system 300 of the preferred embodiment and variations thereof can be embodied and/or implemented at least in part as a machine configured to receive a computer-readable medium storing computer-readable instructions. The instructions are preferably executed by computer-executable components preferably integrated with the system 300 and one or more portions of the processor 320 and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The figures illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals will recognize from the previous detailed description and from the figures and claims, modifications and changes can be made to the preferred embodiments of the invention without departing from the scope of this invention defined in the following claims.

I claim:

1. A method for providing and aggregating EEG bioelectrical signal data, using a first EEG biosignal neuroheadset and a second EEG biosignal neuroheadset, the method comprising:
    establishing a first electrical interface between the first EEG biosignal neuroheadset and a body region of a first user proximal a head region of the first user;
    establishing a second electrical interface between the second EEG biosignal neuroheadset and a body region of a second user proximal a head region of the second user;
    providing a stimulus to the first user and to the second user, wherein the stimulus is configured to prompt an action in both the first user and the second user;
    at a first EEG sensor system of the first EEG biosignal neuroheadset, automatically collecting a first EEG bioelectrical signal dataset from the first user as the first user performs the action;
    at a first motion sensor system of the first EEG biosignal neuroheadset, collecting a first motion dataset from the first user as the first user performs the action;
    at a second EEG sensor system of the second EEG biosignal neuroheadset, automatically collecting a second EEG bioelectrical signal dataset from the second user as the second user performs the action;
    at a second motion sensor system of the second EEG biosignal neuroheadset, collecting a second motion dataset from the second user as the second user performs the action;
    generating a first anonymized EEG bioelectrical signal dataset from the first EEG bioelectrical signal dataset and a second anonymized EEG bioelectrical signal dataset from the second EEG bioelectrical signal dataset;
    coupling the first and the second anonymized EEG bioelectrical signal datasets with an action tag characterizing the action; and
    generating an analysis based upon the first and the second motion datasets and the first and the second anonymized EEG bioelectrical signal datasets, wherein the analysis facilitates elicitation of target brain activity.

2. The method of claim 1, wherein providing a stimulus comprises providing the stimulus at a first mobile device of the first user and providing the stimulus at a second mobile device of the second user.

3. The method of claim 1, wherein providing a stimulus comprises automatically providing the stimulus in synchronization with additional biosignal data collected from at least one of the first user and the second user.

4. The method of claim 1, wherein automatically collecting a first bioelectrical signal dataset from the first user as the first user performs the action and automatically collecting a second bioelectrical signal dataset from the second user as the second user performs the action comprise automatically detecting when the first user and the second user initiate performance of the action, automatically detecting when the first user and the second user terminate performance of the action, and collecting the first and the second bioelectrical signal dataset between initiation and termination of the action for each of the first user and the second user.

5. The method of claim 4, wherein automatically detecting comprises automatically detecting at a sensor system configured to receive at least one of biosignal data and environment data.

6. The method of claim 1, further comprising:
providing a second stimulus configured to prompt a second action in both the first user and the second user;
at the first biosignal detector, automatically collecting a first repeat bioelectrical signal dataset from the first user as the first user performs the second action; and
at the second biosignal detector, automatically collecting a second repeat bioelectrical signal dataset from the second user as the second user performs the second action.

7. The method of claim 6, further comprising generating a comparative analysis based upon at least two of the first bioelectrical signal dataset, the second bioelectrical signal dataset, the first repeat bioelectrical signal dataset, and the second repeat bioelectrical signal dataset.

8. The method of claim 6, wherein the stimulus is identical to the second stimulus.

9. The method of claim 1, wherein generating an analysis comprises generating a comparative analysis characterizing a demographic group comprising the first user and the second user.

10. The method of claim 1, wherein the first EEG sensor system comprises a first plurality of EEG sensors corresponding to a first plurality of channels, wherein the first EEG bioelectrical signal dataset comprises first multi-channel EEG bioelectrical signal data, wherein the second EEG sensor system comprises a second plurality of EEG sensors corresponding to a second plurality of channels, wherein the second EEG bioelectrical signal dataset comprises second multi-channel EEG bioelectrical signal data, and wherein generating the analysis comprises generating the analysis based on the first and the second motion datasets and the first and the second multi-channel EEG bioelectrical signal datasets.

11. The method of claim 10, wherein the first motion sensor system comprises a first accelerometer and a first gyroscope, wherein the first motion dataset comprises first accelerometer data and first gyroscope data, wherein the second motion sensor system comprises a second accelerometer and a second gyroscope, and wherein the second motion dataset comprises second accelerometer data and second gyroscope data, and wherein generating the analysis comprises generating the analysis based upon the first and the second accelerometer data, the first and the second gyroscope data, and the first and the second multi-channel EEG bioelectrical signal datasets.

12. The methd of claim 1, wherein coupling the first and the second anonymized EEG bioelectrical signal datasets with the action tag comprises coupling the first and the second anonymized EEG bioelectrical signal datasets with the action tag based on the first and the second motion datasets.

13. A method for providing and aggregating bioelectrical signal data, using a EEG biosignal neuroheadset, the method comprising:
defining a first action and a second action;
at a first EEG sensor system of the EEG biosignal neuroheadset, automatically collecting a first bioelectrical signal dataset from a first user as the first user performs the first action and automatically collecting a second bioelectrical signal dataset from the first user as the first user performs the second action;
at a motion sensor system of the EEG biosignal neuroheadset, collecting a first motion dataset from the first user as the first user performs the first action and collecting a second motion dataset from the first user as the first user performs the second action;
generating a first anonymized bioelectrical signal dataset from the first bioelectrical signal dataset and a second anonymized bioelectrical signal dataset from the second bioelectrical signal dataset;
coupling the first anonymized bioelectrical signal dataset with a first action tag characterizing the first action and the second anonymized bioelectrical signal dataset with a second action tag characterizing the second action;
generating an analysis based upon the first and the second motion datasets first and the second anonymized bioelectrical signal datasets.

14. The method of claim 13, wherein defining the first action and the second action comprise providing a first stimulus configured to prompt the first action by the user and providing a second stimulus configured to prompt the second action by the user.

15. The method of claim 13, wherein automatically collecting a first bioelectrical signal dataset from a first user as the first user performs the first action comprises automatically detecting when the first user initiates performance of the first action, automatically detecting when the first user terminates performance of the action, and collecting the first bioelectrical signal dataset between initiation and termination of the first action.

16. The method of claim 13, further comprising collecting a baseline bioelectrical signal dataset, and normalizing at least one of the first bioelectrical signal dataset and the second bioelectrical signal dataset using the baseline bioelectrical signal dataset.

17. The method of claim 13, further comprising adjusting an environment of the user based upon the analysis.

18. The method of claim 13, wherein the first action is substantially identical to the second action.

19. The method of claim 13, wherein generating an analysis comprises generating a comparison between the first bioelectrical signal dataset and the second bioelectrical signal dataset based upon signal analysis and data mining.

20. A system for providing and aggregating bioelectrical signal data comprising:
a first EEG biosignal neuroheadset for collecting a first bioelectrical signal dataset and a first motion dataset from the first user as the user performs an action, wherein the first EEG biosignal neuroheadset comprises:
a first EEG sensor system for collecting the first bioelectrical signal dataset; and a first motion sensor system for collecting the first motion dataset;

a second EEG biosignal neuroheadset for collecting a second bioelectrical signal dataset and a second motion dataset from the second user as the user performs the action, wherein the second EEG biosignal neuroheadset comprises:

a second EEG sensor system for collecting the second bioelectrical signal dataset; and a second motion sensor system for collecting the second motion dataset a remote server comprising:

a receiver for receiving the first and the second bioelectrical signal datasets, an anonymizer for transforming the first bioelectrical signal dataset and the second bioelectrical signal dataset into a first and a second anonymized bioelectrical signal dataset, a coupler for coupling the first anonymized bioelectrical signal dataset with an action tag characterizing the action, and to couple the second anonymized bioelectrical signal dataset with the action tag, and an analyzer to for generating an analysis based upon the first and the second motion datasets and the first and the second anonymized bioelectrical signal dataset.

21. The system of claim 20, wherein at least one of the first biosignal detector and the second biosignal detector comprises a sensor system configured to automatically sense an indicator of the action.

22. The system of claim 21, wherein the sensor system comprises at least one of a GPS sensor, an accelerometer, and an optical sensor.

23. The system of claim 20, wherein the first biosignal detector and the second biosignal detector comprise personal electroencephalogram signal collection devices.

* * * * *